US012698319B2

(12) United States Patent
Rye et al.

(10) Patent No.: US 12,698,319 B2
(45) Date of Patent: Aug. 4, 2026

(54) PEPTIDES FOR BETA-CELL SURVIVAL AND INSULIN PRODUCTION

(71) Applicants: Protean Bio, Inc., Lexington, MA (US); University of New South Wales, Sydney (AU)

(72) Inventors: Kerry-Anne Rye, Sydney (AU); Madhav Devalaraja, Lexington, MA (US); Maté Biro, Sydney (AU); Blake Cochran, Sydney (AU); Thomas King, Sydney (AU); Szun Tay, Sydney (AU); Feyza Colakoglu, Sydney (AU); Vanesaa Prajitno, Sydney (AU)

(73) Assignees: Protean Bio, Inc.; University of New South Wales, Sydney (AU)

( * ) Notice: Subject to any disclaimer, the term of this patent is extended or adjusted under 35 U.S.C. 154(b) by 0 days.

(21) Appl. No.: 19/323,294

(22) Filed: Sep. 9, 2025

(65) Prior Publication Data

US 2026/0008836 A1     Jan. 8, 2026

Related U.S. Application Data

(63) Continuation of application No. 18/446,009, filed on Aug. 8, 2023, now abandoned.

(60) Provisional application No. 63/395,860, filed on Aug. 7, 2022.

(51) Int. Cl.
　　*C07K 14/775*　　(2006.01)
　　*A61P 37/02*　　(2006.01)
(52) U.S. Cl.
　　CPC ............ *C07K 14/775* (2013.01); *A61P 37/02* (2018.01)
(58) Field of Classification Search
　　None
　　See application file for complete search history.

(56) References Cited

U.S. PATENT DOCUMENTS

| | | |
|---|---|---|
| 6,972,290 B2 | 12/2005 | Bauman et al. |
| 8,298,537 B2 | 10/2012 | Feldmann et al. |
| 8,703,718 B2 | 4/2014 | Cohen et al. |
| 8,722,632 B2 | 5/2014 | Cohen et al. |
| 8,828,998 B2 | 9/2014 | Palombella et al. |
| 8,926,975 B2 | 1/2015 | Wong et al. |
| 9,605,066 B2 | 3/2017 | Osterroth et al. |
| 9,751,940 B2 | 9/2017 | Smith et al. |
| 9,822,400 B2 | 11/2017 | Dennis et al. |
| 9,907,765 B2 | 3/2018 | Weidner et al. |
| 10,113,198 B2 | 10/2018 | Begovich et al. |
| 10,555,913 B2 | 2/2020 | Brentzel et al. |
| RE48,370 E | 12/2020 | Dillon et al. |
| 10,864,285 B2 | 12/2020 | Chiorini et al. |
| 11,136,372 B2 * | 10/2021 | Remaley ............ A61K 38/1709 |
| 11,827,690 B2 | 11/2023 | Remaley et al. |
| 2016/0251424 A1 | 9/2016 | Wong et al. |

| | | |
|---|---|---|
| 2016/0280776 A1 | 9/2016 | Medich et al. |
| 2017/0087156 A1 | 3/2017 | Allen et al. |
| 2017/0157249 A1 | 6/2017 | Kupper et al. |
| 2017/0165266 A1 | 6/2017 | Gandhi et al. |
| 2017/0333418 A1 | 11/2017 | Hallak et al. |
| 2018/0050031 A1 | 2/2018 | Kaye |
| 2019/0002575 A1 | 1/2019 | Martin et al. |
| 2019/0231848 A1 | 8/2019 | Rotman et al. |
| 2020/0131245 A1 | 4/2020 | Birks et al. |
| 2020/0209237 A1 | 7/2020 | Mozaffarian et al. |
| 2020/0222413 A1 | 7/2020 | Elmore et al. |
| 2020/0283499 A1 | 9/2020 | Schmitz et al. |
| 2021/0177966 A1 | 6/2021 | Mpofu |
| 2021/0206869 A1 | 7/2021 | Smith et al. |
| 2021/0230719 A1 | 7/2021 | Huang et al. |
| 2022/0041720 A1 | 2/2022 | Leon et al. |

FOREIGN PATENT DOCUMENTS

| | | |
|---|---|---|
| WO | 2018/136803 A1 | 7/2018 |
| WO | 2023/039295 A1 | 3/2023 |
| WO | 2023/044495 A2 | 3/2023 |

OTHER PUBLICATIONS

Jung. Targeted Immunotherapy for Autoimmune Disease. Immune Netw; 22(1):1-23. (Year: 2022).*
Wolska. A dual apolipoprotein C-II mimetic-apolipoprotein C-III antagonist peptide lowers plasma triglycerides. Sci Transl Med; 12(258):eaaw7905 (Year: 2020).*
Gupta et al. Renegade homeostatic cytokine responses in T1D: Drivers of regulatory/effector T cell imbalance. Clin Immunol, 2014; 151: 146-154. (Year: 2014).
Prajitno et al. Effect of SARS-CoV-2 on pancreatic B-cell dysfunction and D6PV as a treatment for type 1 diabetes. Presentation Abstract, 2021; TSP Conference, UNSW Sydney. (Year: 2021).
Wolska et al. Apolipoprotein Mimetic Peptides: Potential New Therapies for Cardiovascular Diseases. Cells, 2021; 10 (597): 1-18. ( Year: 2021).
Beik et al. Prevention of Type 1 Diabetes: Past Experiences and Future Opportunities. J Clin Med, 2020 (9)2805: 1-22 (Year: 2020).
Pihoker et al. Autoantibodies in Diabetes. Diabetes, 2005; 54(suppl_2):S52-S61 (Year: 2005).
Holmberg et al. Lowering apolipoprotein CIII delays onset of type 1 diabetes. PNAS, 2011; 108(26): 10685-10689 (Year: 2011).
Fick et al. Severe hypertriglyceridemia at new onset type 1 diabetes mellitus. J Pediatric Endocrinol Metabl, 2017; 30 (8):893-897 ( Year: 2017).
Diagnosis and Classification of Diabetes Mellitus. Diabetes Care, 2014; 37(s1):s81-s91 (Year: 2014).

* cited by examiner

*Primary Examiner* — Daniel E Kolker
*Assistant Examiner* — Maureen Varina Driscoll
(74) *Attorney, Agent, or Firm* — Davé Law Group, LLC; Raj S. Davé

(57) ABSTRACT

A method to prevent a disease, comprising: (1) administering a peptide comprising Delta6PV into a subject comprising a human or an animal; wherein the disease comprises one of more of Type 1 diabetes, rheumatoid arthritis, lupus, Sjogren's syndrome, multiple sclerosis, Graves' disease, giant cell arteritis, ankylosing spondylitis, and Guillain Barre Syndrome; and (2) monitoring the disease in the subject.

19 Claims, 12 Drawing Sheets
(12 of 12 Drawing Sheet(s) Filed in Color)

PEPTIDES FOR BETA-CELL SURVIVAL AND INSULIN PRODUCTION

RELATED APPLICATION

This application is a continuation application of U.S. Ser. No. 18/446,009, titled "PEPTIDES FOR BETA-CELL SURVIVAL AND INSULIN PRODUCTION", filed on Aug. 8, 2023, which claims priority from U.S. Application No. 63/395,860 titled, "PEPTIDES FOR BETA-CELL SURVIVAL AND INSULIN PRODUCTION" filed on Aug. 8, 2022, which are incorporated by reference in their entirety. This application relates to U.S. Pat. No. 11,136,372 B2 titled as, "APOC-II MIMETIC PEPTIDES," which is incorporated by reference in its entirety.

FIELD OF THE INVENTION

This invention relates to the peptide and a process of developing a peptide that increases expression of a gene that is essential for beta-cell survival and increases insulin production and secretion in the Ins1-E insulinoma cell line.

SUMMARY OF INVENTION

An embodiment relates to a method to prevent a disease, comprising: (1) administering a peptide comprising Delta6PV into a subject comprising a human or an animal; wherein the disease comprises one of more of Type 1 diabetes, rheumatoid arthritis, lupus, Sjogren's syndrome, multiple sclerosis, Graves' disease, giant cell arteritis, ankylosing spondylitis, and Guillain Barre Syndrome; and (2) monitoring the disease in the subject.

An embodiment relates to a method to treat a disease, comprising: (1) administering a peptide comprising Delta6PV into a subject comprising a human or an animal; wherein the disease comprises one of more of Type 1 diabetes, rheumatoid arthritis, lupus, Sjogren's syndrome, giant cell arteritis, multiple sclerosis, Graves' disease, ankylosing spondylitis, and Guillain Barre Syndrome; and (2) monitoring the disease in the subject.

In an embodiment, the peptide is configured to improve insulin sensitity, C peptide, glucose levels and HbA1C in Type 1 diabetes patients In an embodiment, the peptide is configured to improve a score count of ACR20, ACR50 and ACR70 in the rheumatoid arthritis.

In an embodiment, the peptide is configured to improve SELENA SLEDAI scores in the lupus.

In an embodiment, the peptide is configured to decrease formation of an auto antibody and reduces inflammation.

In an embodiment, the peptide is configured to reduce numbness in limbs and increases mobility in limbs.

In an embodiment, the peptide is configured to increase thyroid secretion.

In an embodiment, the peptide is configured to improve the AS40 scores in the Ankylosing spondylitis.

In an embodiment, the peptide is configured to inhibit IL-2 or IL-7 or IL-15 driven expansion of primary human T cells.

In an embodiment, the peptide is configured to inhibit primary CD8 T cell expansion.

In an embodiment, the peptide is configured not to impair the T cell cytotoxicity.

An embodiment relates to the influence of D6PV on primary T cell expansion and function.

In an embodiment, D6PV does not significantly impair naïve T cell activation.

In an embodiment, D6PV does not impair primary murine T cell cytotoxicity.

In an embodiment, D6PV significantly restricts primary murine T cell expansion.

In an embodiment, the inhibitory effect of D6PV on expansion is specific to T cells.

In an embodiment, human CD4+ and CD8+ T cell expansions are severely inhibited by D6PV.

In one embodiment, a pharmaceutical composition comprising a peptide, an additive and a pharmaceutically acceptable carrier; wherein the peptide is D6PV; wherein the pharmaceutical composition is configured to increase expression of beta-cell, production of insulin.

In one embodiment, a process to delay onset of type 1 diabetes, comprising: inserting 35-45 mg/Kg D6PV twice a week, into a subject; evaluating glucose level of the subject; increasing the dose of the subject per week.

In one embodiment, a process to improve glycaemic control, comprising: inserting 35-45 mg/Kg D6PV twice a week, into a subject; evaluating glucose level of the subject; increasing the dose of the subject per week.

In one embodiment, a method of use of pharmaceutical composition comprising injecting the pharmaceutical composition into an animal.

BRIEF DESCRIPTION OF THE FIGURES

The patent or patent application file contains at least one drawing executed in color. Copies of this patent or patent application publication with color drawing(s) will be provided by the Office upon request and payment of the necessary fee.

DETAILED DESCRIPTION

Definitions and General Techniques

Figure 1:
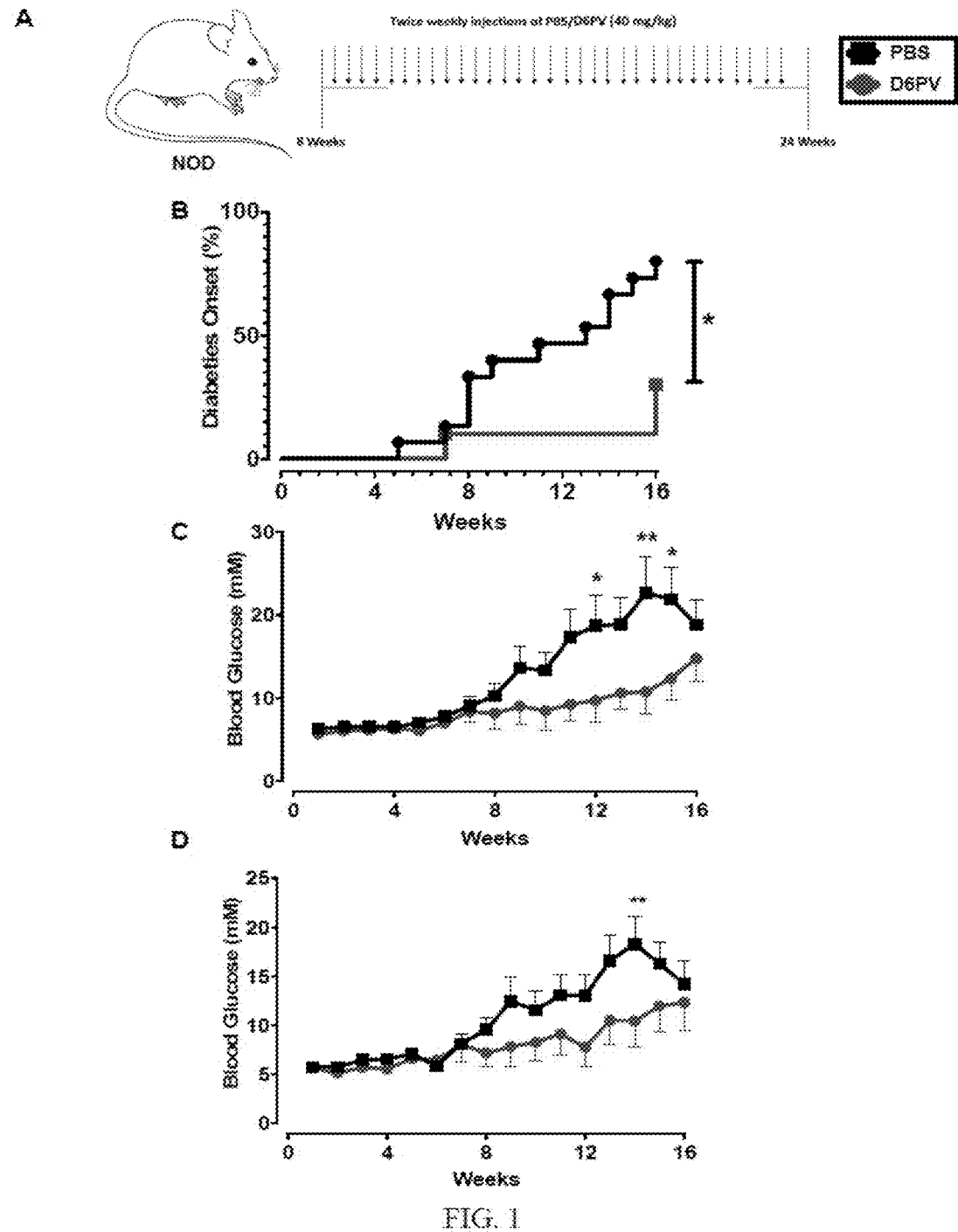
FIG. 1 shows D6PV treatment delays the onset of a diabetic phenotype in NOD mice and decreases fed and fasting blood glucose levels. (A) 8-week-old NOD were randomised to receive D6PV (40 mg/kg, i.p) or an equal volume of PBS (i.p) twice weekly for 16 weeks. (B) The onset of diabetes was determined by two consecutive fed blood glucose readings >13.5 mM over two consecutive days. Data is displayed as a Kaplan-Meier Survival curve. (C) represents fed blood glucose levels and (D) represents 5 h fasted blood glucose levels. Results are presented as mean #SEM and analysed using 2-way ANOVA-mixed effect analysis and Log-rank (Mantel-Cox) test where appropriate. * $p<0.05$, ** $p<0.01$.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denotes the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real time" encompasses operations that occur in "near" real time or somewhat delayed from a triggering event. In a number of embodiments, "real time" can mean real time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

As used herein, the term "peptide" refers a short polymer of amino acids linked together by peptide bonds. In contrast to other amino acid polymers (e.g., proteins, polypeptides, etc.), peptides are of about 75 amino acids or less in length. A peptide can comprise natural amino acids, non-natural amino acids, amino acid analogs, and/or modified amino acids. A peptide can be a subsequence of naturally occurring protein or a non-natural (synthetic) sequence.

As used herein, the term "mutant peptide" refers to a variant of a peptide having a distinct amino acid sequence from the most common variant occurring in nature, referred to as the "wild-type" sequence. A mutant peptide can comprise one or more amino acid substitution, deletion, or insertion as compared to the wild-type sequence. A mutant peptide can be a subsequence of a mutant protein or polypeptide (e.g., a subsequence of a naturally-occurring protein that is not the most common sequence in nature), or can be a peptide that is not a subsequence of a naturally occurring protein or polypeptide. For example, a "mutant apoC-II peptide" can be a subsequence of a mutant version of apoC-II or can be distinct sequence not found in naturally-occurring apoC-II proteins.

As used herein, the term "synthetic peptide" refers to a peptide having a distinct amino acid sequence from those found in natural peptides and/or proteins. A synthetic protein is not a subsequence of a naturally occurring protein, either the wild-type (i.e., most abundant) or mutant versions thereof. For example, a "synthetic apoC-II peptide" is not a subsequence of naturally occurring apoC-II. A "synthetic peptide," as used herein, can be produced, or synthesized by any suitable method (e.g., recombinant expression, chemical synthesis, enzymatic synthesis, etc.).

The terms "peptide mimetic" or "peptidomimetic" refer to a peptide-like molecule that emulates a sequence derived from a protein or peptide. A peptide mimetic or peptidomimetic can contain amino acids and/or non-amino acid components. Examples of peptidomimetics include chemically modified peptides, peptoids (side groups are appended to the nitrogen atom of the peptide backbone, rather than to the α-carbons), β-peptides (amino group bonded to the β carbon rather than the α-carbon), etc. Chemical modification includes one or more modifications at amino acid side groups, α-carbon atoms, terminal amine group, or terminal carboxy group. A chemical modification can be adding chemical moieties, creating new bonds, or removing chemical moieties. Modifications at amino acid side groups include, without limitation, acylation of lysine &-amino groups, N-alkylation of arginine, histidine, or lysine, alkylation of glutamic or aspartic carboxylic acid groups, lactam formation via cyclization of lysine ¿-amino groups with glutamic or aspartic acid side group carboxyl groups, hydrocarbon "stapling" (e.g., to stabilize alpha-helix conformations), and deamidation of glutamine or asparagine. Modifications of the terminal amine group include, without limitation, the desamino, N-lower alkyl, N-di-lower alkyl, constrained alkyls (e.g., branched, cyclic, fused, adamantyl) and N-acyl modifications. Modifications of the terminal carboxy group include, without limitation, the amide, lower alkyl amide, constrained alkyls (e.g., branched, cyclic, fused, adamantyl) alkyl, dialkyl amide, and lower alkyl ester modifications. Lower alkyl is C1-C4 alkyl. Furthermore, one or more side groups, or terminal groups, can be protected by protective groups known to the ordinarily skilled peptide chemist. The α-carbon of an amino acid can be mono- or dimethylated. As used herein, the term "subject" broadly refers to any animal, including but not limited to, human and non-human animals (e.g., dogs, cats, cows, horses, sheep, pigs, poultry, fish, crustaceans, etc.). As used herein, the term "patient" typically refers to a subject that is being treated for a disease or condition.

As used herein, the term "effective amount" refers to the amount of a composition (e.g., a synthetic peptide) sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment (e.g., synthetic peptide) to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal or lingual), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., multiple synthetic peptides or a synthetic peptide and another therapeutic agent) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used can vary. The appropriate dosage for co-administration can be readily determined by one skilled in the art. In some embodiments, when agents or therapies are coadministered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "treatment" means an approach to obtaining a beneficial or intended clinical result. The beneficial or intended clinical result can include alleviation of symptoms, a reduction in the severity of the disease, inhibiting an underlying cause of a disease or condition, steadying diseases in a non-advanced state, delaying the progress of a disease, and/or improvement or alleviation of disease conditions.

As used herein, the term "pharmaceutical composition" refers to the combination of an active agent (e.g., apoC-II mimetic peptide) with a carrier, inert or active, making the composition especially suitable for therapeutic or diagnostic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), glycerol, liquid polyethylene glycols, aprotic solvents such as dimethylsufoxide, N-methtylpyrrolidone and mixtures thereof, and various types of wetting agents, solubilizing agents, anti-oxidants, bulking agents, protein carriers such as albumins, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 21th Ed., Mack Publ. Co., Easton, Pa. (2005), incorporated herein by reference in its entirety.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

The following terms and phrases, unless otherwise indicated, shall be understood to have the following meanings.

An embodiment relates to interventions that regenerate functional pancreatic beta-cells are a novel treatment option for people with type 1 diabetes. A peptide has been developed that increases expression of a gene that is essential for beta-cell survival and increases insulin production and secretion in the Ins1-E insulinoma cell line. This study asks whether this peptide regenerates beta-cells and/or preserves beta-cell mass in mice with autoimmune beta-cell loss.

Diabetes onset was evaluated in 8-week-old female NOD mice that were treated twice weekly with D6PV (40 mg/kg i.p.) or PBS for 16 weeks (n=10-20/group). A separate cohort of female NOD mice (n=10-15/group) were treated with D6PV or PBS twice weekly for 4 weeks after they developed diabetes. Glycemic control was evaluated by intraperitoneal glucose tolerance test (1 g/kg glucose). Insulin content of paraffin-embedded-formalin-fixed pancreatic tissues was quantified by immunostaining.

In an embodiment, D6PV treatment delayed diabetes onset in NOD mice (p<0.01) and decreased fed and fasted blood glucose levels (p<0.01). D6PV treatment improved glucose tolerance in diabetic NOD mice (p<0.01).

In another embodiment, D6PV improves glycemic control in an autoimmune mouse model of type 1 diabetes.

Materials and Methods

Animal Studies

All animal experimental protocols were approved by the UNSW animal Care and Ethics Committee (20/53A) and conducted in accordance with the Australian Code for the Care and Use of Animals for Scientific Purpose (8th edition 2013). Mice were caged in groups of five in the Lowy Animal Facility (UNSW, Sydney, Australia) in a pathogen free environment.

In an embodiment, to determine if D6PV prevents the development of diabetes in NOD mice, 6-week-old female NOD mice were obtained from the Animal Resource Centre (Perth, Western Australia) and acclimatized for one week. At 8-weeks-old mice were randomized to receive either D6PV (40 mg/kg, i.p.) or an equal volume of PBS twice weekly for 16 weeks. Fed and 5 h fasted blood glucose levels were measured weekly. Diabetes onset was defined as two consecutive fed blood glucose measurements ≥13.5 mM. The mice were euthanized via cardiac puncture and cervical dislocation while under isoflurane anesthesia at study completion.

In an embodiment, to determine if D6PV can improve glycemic control in type 1 diabetes, NOD mice were aged until confirmation of a diabetic phenotype as described above (two consecutive fed blood glucose measurements ≥13.5 mM). Animals which achieved this threshold (n=13-16/group) were randomized to receive D6PV (40 mg/kg i.p.) or an equivalent volume PBS twice weekly for 4 weeks. The mice were then euthanized via cardiac puncture and cervical dislocation while under isoflurane anesthesia.

Intraperitoneal Glucose Tolerance and Insulin Tolerance Tests

Intraperitoneal glucose tolerance tests (IPGTT) were conducted 24 h following the final D6PV or PBS injection. Mice were fasted for 5 h prior to receiving a bolus of D-glucose (1 g/kg i.p). Blood glucose levels were measured with a handheld glucometer at t=0, 15, 30, 45, 60, 90 and 120 min (Accu-Check Performa Nano, Roche).

Insulin Tolerance Tests (ITT) were conducted 24 h after the final D6PV or PBS injection. Random fed mice were injected with human insulin in PBS (1 U/kg, i.p). Blood glucose levels were measured from the tail tip using a handheld glucometer (Accu-Check Performa Nano, Roche) at t=0, 15, 30, 45, 60, 90 and 120 min.

In an embodiment, for type one diabetes there's nothing at all in terms of doing other anything other than supplementing people with insulin to alleviate symptoms, whereas what is in the present specification is finding a way to regenerate insulin producing cells in the pancreas. In an embodiment, the peptide delays the development of diabetes in the gold standard mouse model. The bottom line is that it will delay the development of diabetes quite significantly. And it will also improve glucose handling in animals that already have established disease. And both of those things are equally important, especially as it's children that are at risk of type one diabetes, there's quite good screening programs, quite accurate biomarkers that can detect these children now.

In an embodiment, for this study, here, what has been done is to use that gold standard mouse model as shown in FIG. 1. In FIG. 1 at 8 weeks, they're usually pretty healthy. They haven't got disease onset yet. So that's when it has been decided to start using the drug compound. And what we did was we gave them two injections a week, and we did a 16 week treatment period. So, what we found over that 16 week period, as you can see, the red line is our basic type-1 diabetes treatments at that time. And it's that 16 weeks, there's a significant delay in the onset of diabetes in the animal cohorts. In the PBS line, only about 20% of the cohort survived while for the basic treatment, it's closer to 70%. So that's quite significant for that time period. And by that time for that animal model you'd expect over, like you've seen with the PBS over 80% of the animals to develop diabetes.

In FIG. 1, on the y axis when we have disease free survival is really not the mortality, but referring to the onset of the disease percentage. So, that's the percentage that don't have diabetes. So, in FIG. 1 it is diabetes onset, but is does not mean mice are dead. But the development of diabetes is delayed.

It is essentially, there is a delay in the number of animals progressing to diabetes over time. So, one of the most important things you can look after this animal model is like measuring blood glucose levels is a good indicator of how well everything's functioning for the animal. The threshold to measure blood glucose level is of more than 13.5 milli-molar over two consecutive days. So, in FIG. 1, panel C, we have on random that blood glucose level. So, this could be we did at the same time every day. But theoretically, the animals have free access to food. So at four weeks, we start getting our significant differences in said blood glucose levels. And that's reprise that weeks, 14 and 15. In panel D, we have fasted blood glucose. So, what we did was we fasted them for five hours. And it gives you more of an indication of how that glucose, is being disposed of. And when we measured those ones, over the 16 weeks, we found that at week 14, it was the most significantly different. What glucose level in the in panel C, suggests that they have diabetes.

So, if we look if we measured them weekly, and anytime we got a reading of like, 13.5 or more, we would take those animals the next day measure them. And if it was more than 13.5, or equal to, then we'd say they've developed diabetes. If reading is more than 13 and a half there, it is hypergly-cemic and insulin is need to take over. It's a common threshold used in this mouse model that has been used before. The same fasting blood glucose here on panel D in FIG. 1. As it can be seen, like a wave six standing instead of sort of getting closer to each other. That's sort of a consequence of like, the technical aspects of the study, in the present specification, we had some animals that were dia-betic for over 10 weeks. So at that point, they're getting pretty morbid. So we had to, you know, reach that endpoint for ethical euthanasia. So it's sort of making the data looks like it's going to meet in the middle. So, on the x axis here in panel D in FIG. 1, there are the weeks zero to 16. And this refers to basically the start of the therapy, right, this did or refers to the start of the therapy and 16 weeks means it's almost 24 weeks of the age of demise. For up to six weeks, D6PV group and PBS do not have visible type-1 diabetes, because their percentage i.e. the concentration of blood glucose is less than 13.5 as as shown in panel B of FIG. 1. hese animals, they tend to tip over most animals tip over eating a certain number of weeks, but it's kind of a little bit inside that window. It's random. It because this is a naturally progressing model, it's not ingest.

Non obese diabetic, most mortal, they start developing diabetes quite early on. And that's what you see in the control mice here in FIG. 1. More than 50% by eight or twelve weeks. you don't see that in the disease experienced treated animals? The most telling thing is sort of that stepwise progression for the PBS treated animals. In FIG. 1, panel B, the last dip In the D6PV treated animals shows the onset of the diabetes in the D6PV treated mice. They're disease free progression earlier on.

For type one diabetes NOD mice are gold standard mice because they have a genetic linkage such that their genetic expression is very similar to what happens in humans. And that's why the community uses them as a model.

Figure 2:
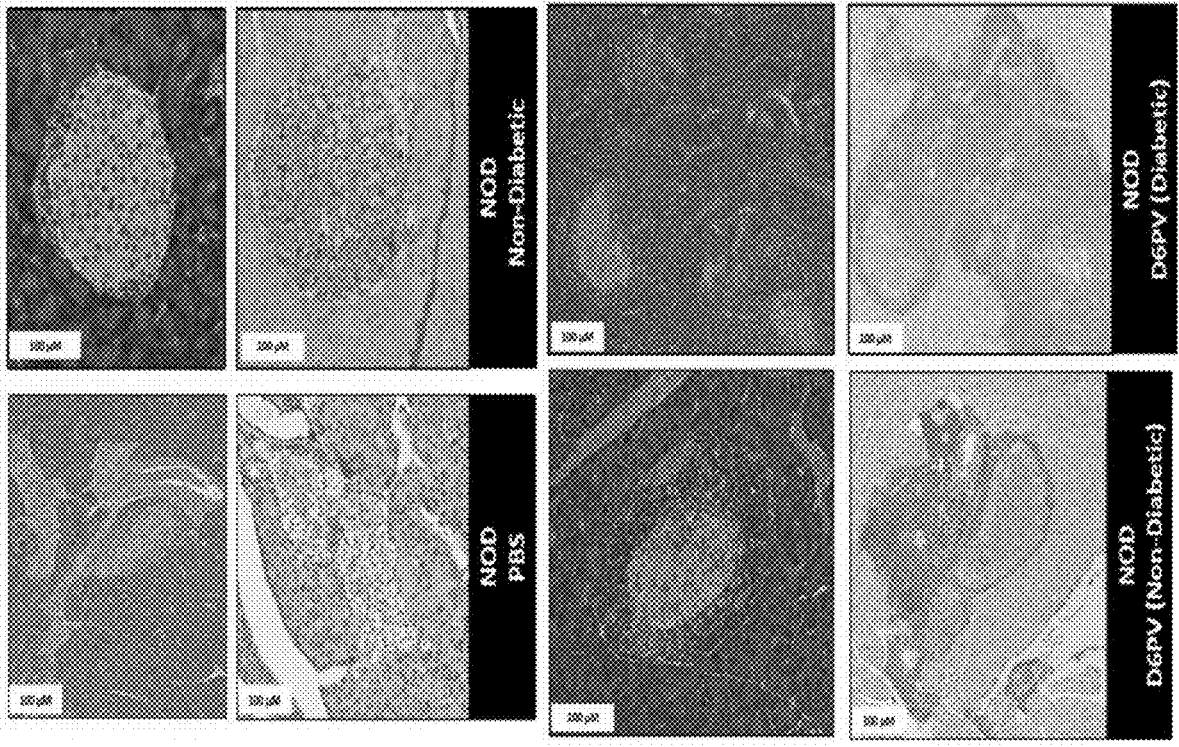
FIG. 2 shows DP6V-treatment increases islet insulin content and lymphocytic infiltration in NOD mice. Pancreata were sectioned, subjected to H&E staining (left panels) and immunostained for insulin (right panels). Images of pancreatic sections from NOD mice that did not develop diabetes (n=5-6/group) (A), PBS-treated NOD mice with diabetes (n=3-5/group) (B), D6PV-treated NOD mice with diabetes (n=3/group) (C) and D6PV-treated NOD mice with insulitis (n=5-6/group) (D) are shown. All data was normalised to the total pancreas area and are presented as mean±SEM and analysed using an unpaired t-test (Welch's Correction). * $p<0.05$.

In FIG. 2, there is a look at the histology of the pancreas of these mice. If you look at the first two panels on the top left hand side, this is what the islets so pancreatic islets full of beta cells, mostly, which are the cells that secrete making secrete insulin. And on the second from the left, top left, you can see this is staining a pancreas for insulin, you can see the brown staining is for insulin, you can see the islets at these, you know, nice, uniform spherical structures before the mice develop diabetes. If we allow the mice to if they progressed to diabetes, and at the end of the study, we euthanize the mice and look at the islets, the mice that were treated to bottom left, so the mice that were treated with PBS, you have the structures that look like islets have no more insulin contained in it anymore. And that's reflective of the fact that the beta cells that were there have been killed. And this happens in an autoimmune manner in this mouse model very similar to what happens in people, which is the reason why we use this mouse model. What you can see is that there's also in this animal here, the NOD-PBS animal, what's happened is that the immune cells have come in have killed the islet have actually left. So we don't even really see many more immune cells there anymore. There's nothing for the immune cells to react to. And we'll take a look at the mice that are treated with D6PV. So, all these mice are at the same time point. The mice that received D6PV that did tip over into diabetes have some standing for insulin. You can see there are some insulin positive areas there but it's not enough or the cells are no longer functional enough to maintain glucose homeostasis in the whole mouse. And you can see especially on the second from right picture, you can see lots of, small grainy blue cells, that's the infiltrating immune cells that are going in and attacking and killing the islets. However, you know this, this is happening later in these mice than if they didn't receive the D6PV at all. So, we're at least delaying the onset of this diabetes, this immune attack. But also, in the mice down the sections down the bottom. This is a mouse that received a D6PV, and by the end of the study had not tipped over into the diabetes. And you can see that there's still you know, there's a lot of insulin standing there. These are still functional beta cells and functional islets that are able to secrete enough insulin to maintain glucose homeostasis, there is some immune cell infiltration, whether or not in these mice that would progress to what you would see in the mouse above, and they'll eventually become diabetic, we don't know. And this is just based on the treatment regime that we gave of, you know, two doses a week, they're not receiving this continuously. So, there's a lot of questions we still have to answer there. The islets still appear pretty normal. They're still the right shape, they're still in the right space, and the actual volume of islets in the hall mouse is comparable to mice that don't develop diabetes at all.

So, the D6PV treated mice in the top versus bottom panel are they're all about 14 weeks, 12 weeks and some control. They're all at that endpoint of the of the treatment. In this study, we didn't euthanize them after a certain number of weeks, we euthanize them all at the end of the study, So they're progressing. into the disease differently every mouse, but we know that for sure that the progression is much slower, whether or not it's totally, you know, never comes in some of those mice, but it's definitely slower in the D6PV treated mice. We're either delaying the onset of the immune cell infiltration, or where if it when it does start, we're slowing it down. We don't know whether or not for example, this bottom right hand mouse, would this mouse if left for longer have progressed into diabetes in FIG. 2. The variability in this phenotype was something that we did not really appreciate when we designed the studies, but it makes the results unexpected. A little challenging, it actually raises a whole lot of questions that we now know, we should be answering. But until you've actually done this and seeing the variability in the way the mice tip over, and some of them will never tip over and some tip over earlier than others. And that's what's is not a confounding factor, but it just makes the interpretation a little bit challenging. I don't know if it is that variable, not most, generally, 80 to 90% don't have diabetes, it may be a matter of, let's say, week 10 versus let's say week 14, but they do develop right? So from that standpoint, variability is not a concern. But the fact that that this D6PV treated ones, almost 70% of them didn't get the diabetes, that shows us something that it's definitely doing what it's doing.

In FIG. 2, these D6PV is perhaps doing two things simultaneously, one is preventing the onset of diabetes. And second, but equally importantly, it's actually preventing what the some of the fundamental pathogenesis that happens, which includes the inflammatory cell influx, and does perhaps preventing the onset of diabetes and maybe third minor point is, it's preserving insulin in that data islets.

IP-GTT is a intraperitoneal glucose tolerance test. It's a test by which the mice are given an injection of glucose and then we monitor the blood glucose over time. And what that allows us to do is to see how well, the mice are able to handle glucose. So, a normal healthy mouse, you give it glucose, the glucose gets rapidly taken up by the various tissues of the mouse. Whereas a diabetic mouse because it can't make as much insulin in response to the glucose, you usually get a much more delayed elimination of glucose from the blood from the bloodstream.

Figure 3:
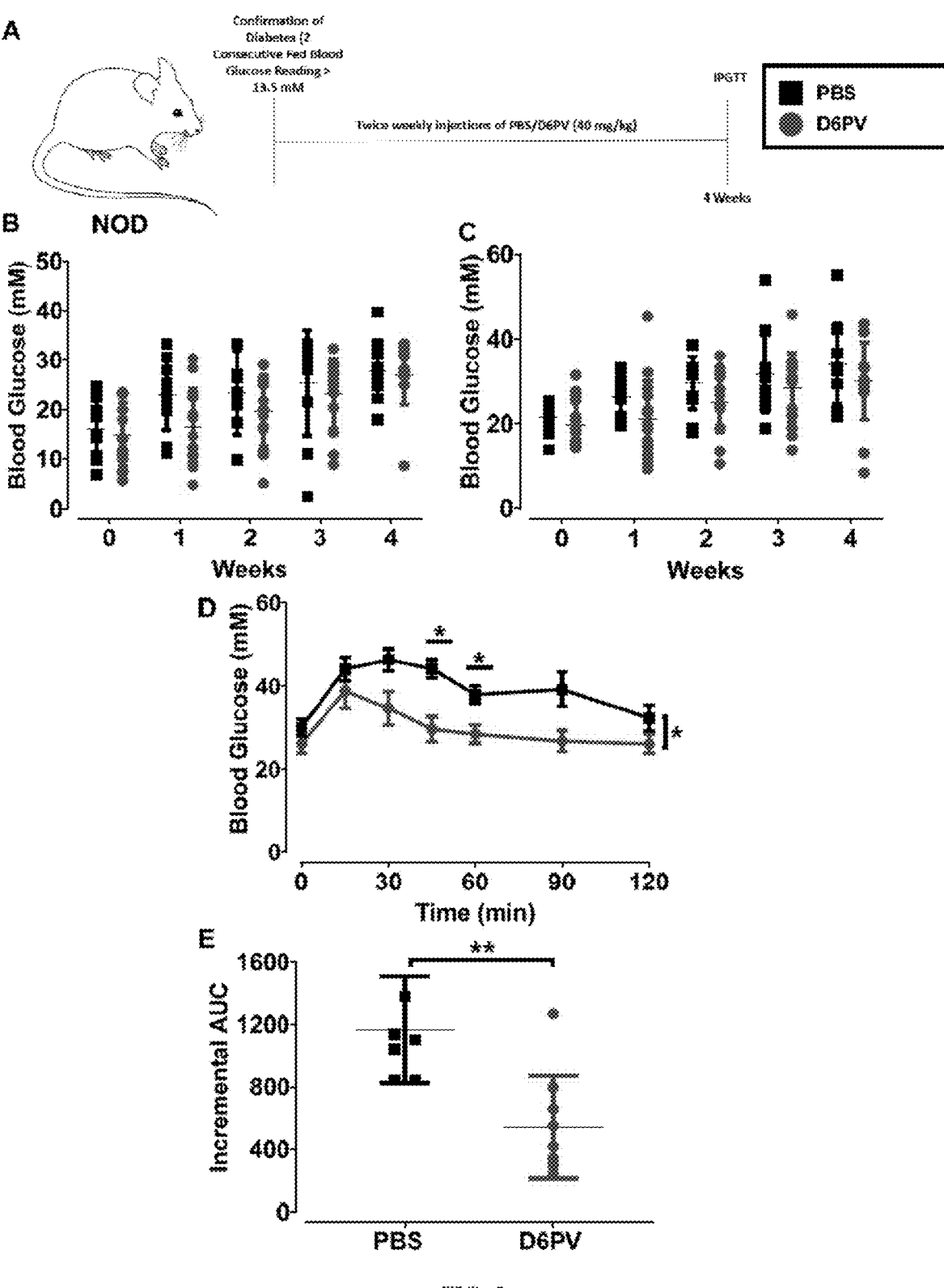
FIG. 3: D6PV treatment improves glucose tolerance in NOD mice with diabetes. (A). NOD mice were aged until diabetes onset which was defined as two consecutive fed blood glucose readings >13.5 mM, then randomised to D6PV (40 mg/kg, i.p, n=15/group) or an equivalent volume of PBS (n=13/group) twice weekly for 4 weeks. Fed blood glucose (B) and 5 hr fasted blood glucose levels (C) were measured weekly. 5 h fasted NOD mice with diabetes were also treated for 4 weeks with D6PV (n=9/group) or PBS (n=7/group) and subjected to an IPGTT (1 g/kg) at 24 h after the final D6PV or PBS injection. Blood glucose levels were quantified at 0, 15, 30, 45, 60, 90 and 120 min (D). Blood was sampled from the lateral tail vein and glucose levels were determined using a handheld glucometer. The incremental AUC is shown in (E). Results are presented as mean±SEM and analysed by 2-way ANOVA with mixed effect analysis and unpaired t-test (Welch's correction). * $p<0.05$, ** $p<0.01$.

In FIG. 3, this study is a complementary study to the previous data that we've shown you. What we did was we allowed the mice to become diabetic first. So, rather than intervene at a certain week, as we did previously, and then look for diabetic progress, we waited until the mice became diabetic. So, when they had two readings, two consecutive daily readings of glucose over 13.5, millimolar. And then we commenced treatment with D6PV peptide. We did that for four weeks and twice per week. And the question we asked there was, once these mice have already tipped over into diabetes, were we able to improve their function. As a result, the blood glucose data in B and C panels, you can see there's not huge differences, there's quite a bit of variability between mice. And these are just fed and fasted blood glucose values. But the really important result from here is, is panel D and then panel D is together with panel A in FIG. 3. And this is the results of a glucose tolerance test. So what it shows is that when we give the injection of glucose intraperitoneally, it then gets into the bloodstream and circulates. The black line is what you would normally expect. And what we see for mice that have only been treated with PBS in that it takes quite a long time for these diabetic NOD-mice to have all the glucose exit their bloodstream and move into their muscle, their adipose tissue, their liver to get metabolized. And that's because they don't have enough insulin circulating. In contrast, the mice that received D6PV, able to much more rapidly metabolize and take the glucose out of the bloodstream and into their tissues. And that's the there is a difference that we say, you can say that there's a significant difference in a couple of time points, specifically after 45 and 60 minutes. And the overall trend in this data is significant. One of the really common ways that we analyze this data is in panel E, is that we look at the area under the curve of the other way map in panel a right down the bottom is that we look at the area under the curve that doesn't let you go that way. So you draw a line underneath and you measure the area under the curve of these responses. This is kind of the way in which this data is analyzed a lot in the literature. And this gives you an ability of the overall it's the blood glucose as a function of time in the mice, and you can say that the mice that received D6PV has significantly improved ability to dispose is the word that we would use but to take up and metabolize glucose. And the reason that this is and we've done some experiments to show is that it's because there is more insulin circulating in the mice in response to glucose. And they suggest that the beta cells are more functional, despite the fact that we only intervened in these mice once they develop diabetes. So it's very it's distinct from our earlier experiment.

So, both of these mice have diabetic mother, either the PBS mice or the D6PV and the difference is that even though it is D6PV treated diabetic, it is able to function better on the untreated mice. We don't have a full understanding of how this, this mechanism occurs yet.

So, in FIG. 3, panels B, or C, so these are the average of those two readings. Because we are injected twice a week. So this, the data in B and C is B is fed, and C is fast blood glucose. So these were just taken once per week from the mice each day and then taken as an average. The reason we've grafted this way is to give you an appreciation that the variability between mice is quite large. And that's okay. That's just the way these mice are. You can may be appreciate this, there is a statistical test that based and have no statistical significance, I don't think but in all of the data points, you can almost see all the time the D6PV mean, the little line is lower than the PBS while. You know, that wouldn't reach statistical significance. But the fact that it's there in every single data point is something interesting, at least. So, we that kind of speaks potentially, to the fact that we are improving their glucose metabolism all the time, not just when we give a glucose challenge.

Data in B, C and D panel of FIG. 3 is different. That's a glucose tolerance test. So that's where we take the mice, we fast them for five hours, we give them an injection of a known amount of glucose based on their body weight. And then we just track them over two hours. This was after the last D6PV or PBS projection. So, it's 24 weeks. This is right at the end. So, at the end of the treatment protocol, and you include it every day D6PV mouse, that was diabetic. So, we get the mice to go diabetic first. And then we treat it half with PBS and half, with D6PV and the data in D is the result of 15 per group.

Variability in these graphs these are standard errors. But even with standard deviations, the significance is based on standard deviations. So you know, even with standard deviations on the graph, it still looks pretty good. When you do the air under the curve, you're accounting for the difference in the baseline as well. So the fact that there's a bit of variability in say, when the mice have fasted, the area under the curve, because we're looking at, we're testing the mouse against its own zero time, point, glucose, so that allows us to control for that variability quite nicely. Yeah, so this is pretty much similar to what we did in the previous study.

Figure 4:
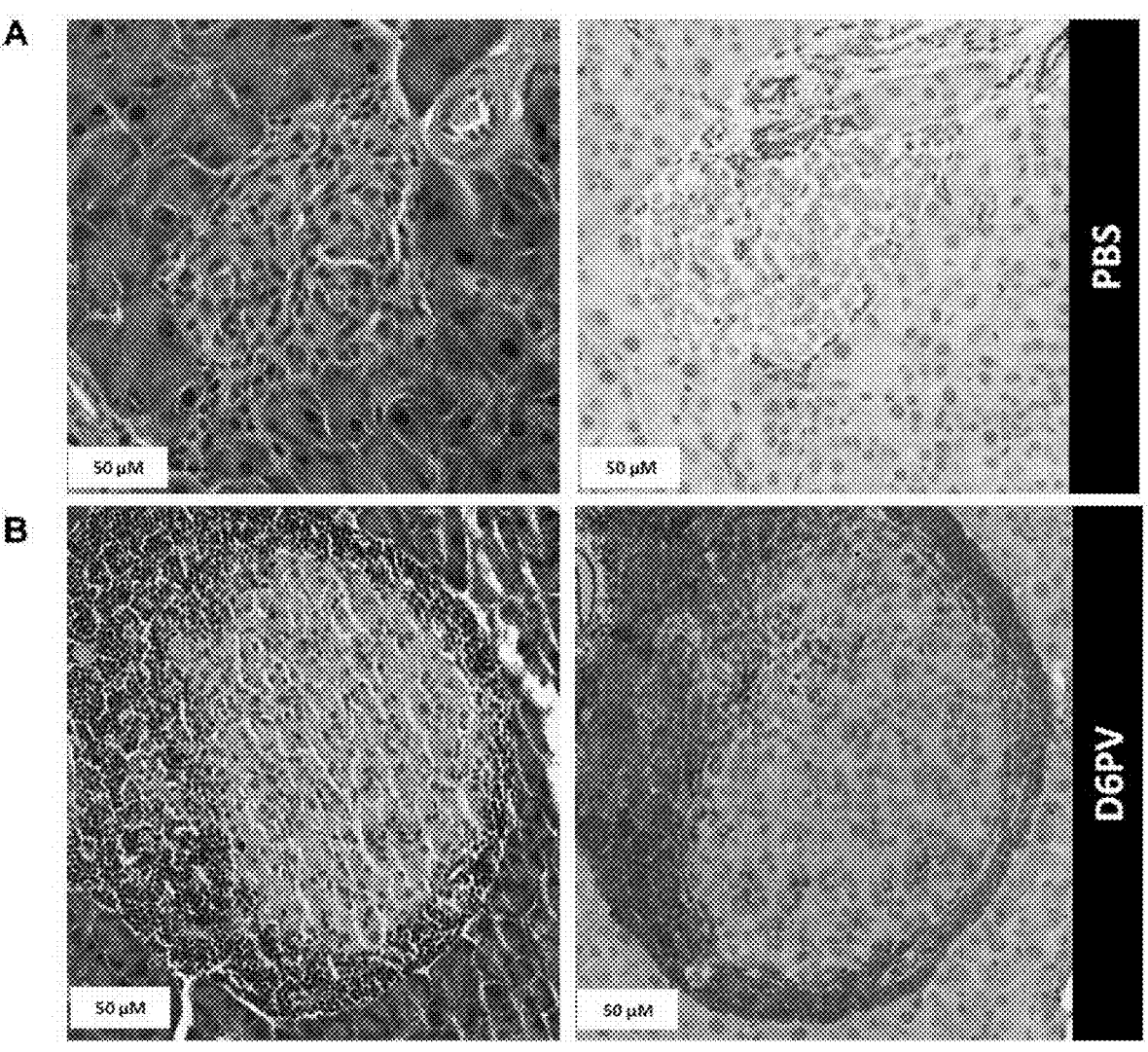
FIG. 4: shows D6PV treatment increases pancreatic insulin levels in NOD mice with confirmed diabetes. Pancreatic sections from NOD mice with diabetes that had been treated with PBS (A) and D6PV (B) were subjected to H&E staining (left panels) and immunostained for insulin (right panels).

In FIG. 4, we looked at the histology, this is pink and red one is called same toxin as and it just gives you an A sense of like the architecture, whereas this brown staining once again, is insulin. So when we directly looked at our PBS animals, which are off the top in our D6PV treated animals, the surprising findings found was that there's quite a lot of insulin in the D6PV treated animals that first developed died of diabetes. And I guess the studies have been more powerful in the sense that we know how long these animals are sick for and I guess it gets rid of some of the variability from the previous study. So even though the fact that we have any insulin at all in like these islets, that's quite impressive for this study. So that's basically what this one showing. So, these are the animals with concern, diabetes and then got our treatment for four weeks. So, these are the prophylactic vs therapeutic approach.

So, these are the disease maps of animals. And so, you know, theoretically there, lymphocytic infiltration, all the immune stuff should be the same. since we've used those thresholds to confirm diabetes and then start treatment. Basically, these animals that are in the staining here, come from this panel D of FIG. 3. So that that provides us sort of a reason that improved glucose tolerance is actually insulin to combat the bolus of glucose and facilitate glucose uptake into the tissues.

The one thing to keep in mind is this is totally observational, so we have no understanding of the mechanism of how this occurs yet. But we are getting well, we are ready to go to do a sort of major, special transcriptomic analysis subsections from these samples. And I think that's going to give us at least some insights as to what's going to be, but we haven't got there yet.

You know, so what we are saying here is, let's say in this and in the previous groups of animals, both ways, we show that there is a decrease inflammatory cell influx in FIG. 4. And consequently, there's a preservation of insulin secreting beta cell. And then by the other data, we are saying that inflammatory cell that we are perhaps mostly affecting is the T cell activation. And that's what we show there. Again, there are two groups of animals that do big experiments. One is try to understand if you use a peptide prophylactically in these animals, would the animal not get the diabetes at all. The second group of animals is that the animal has the diabetes and then you do the peptide, what happens right? So, in both scenarios, D6PV peptide here being discussed significantly affects either the onset of diabetes, progression of diabetes and then the mechanisms that we did through the mechanisms that we discussed. D6PV is a new novel peptide that we created that has got an antagonistic function of a molecule called apoC-III and antagonize apoC-II, it has got a dual functionality. so that peptides having these kinds of effects in a diabetes setting. apoC-II and apoC-III are only involved in triglyceride clearance. And so those mechanisms and this peptide having an effect in diabetes is quite novel.

The mice were not insulin resistant. They have normal insulin sensitivity, and certainly an another mouse model where we've looked at D6PV, we've not seen any, any impact at all on insulin sensitivity. PBS animals would be theoretically more insulin sensitive if they don't have insulin. So it could be a good thing to show.

One is method to prevent diabetes. Second is method to treat diabetes. And with respect to the two methods of preventing diabetes. The onset with in the mice which were treated with the peptide versus the treated with the placebo, there is a difference in the time. It is very clear that a person skilled in the art would recognize that this peptide with it because it's tested on my particular type of mice that has a one to one relationship with humans that it could also work on humans.

In an embodiment, the peptide is configured to prevent and treat following diseases are known to be mediated by activated T cells.

Rheumatoid arthritis: monitored by ACR20, ACR50 and ACR70 disease scores. Improvement in the score is considered as betterment of the disease Lupus: monitored by SELENA SLEDAI scores. Improvement in these scores is what we want with therapy Sjogren's syndrome: Decrease auto antibody formation, inflammation and the symptoms.

Multiple Sclerosis: Improvements in mobility, pain, numbness, tingling, fatigue, depression, anxiety etc.

Graves' disease: Improvement in thyroid secretion, eye disease

Ankylosing spondylitis: Improvements in AS40 scores and the flare of the disease Guillian Barre Syndrome: Improvement in pain, vision, gait, tingling sensation and various other symptoms.

Table below provides a list of disease and their treatment methods. All patent publications are incorporated in its entirety.

| Diseases | Patent No. and Name |
|---|---|
| Rheumatoid arthritis: monitored by ACR20, ACR50 and ACR70 disease scores. Improvement in the score is considered as betterment of the disease. | 1. US20170157249A1-Uses and compositions for treatment of rheumatoid arthritis. 2. US20160280776A1-Uses and Compositions for Treatment of Juvenile Rheumatoid Arthritis. 3. U.S. Pat. No. 8,703,718B2-Methods for treating juvenile rheumatoid arthritis by administering a soluble CTLA4 molecule. 4. U.S. Pat. No. 9,822,400B2-Methods for treating, diagnosing, and monitoring rheumatoid arthritis 5. US20210230719A1-Compositions for the treatment of rheumatoid arthritis and methods of using same 6. U.S. Pat. No. 8,298,537B2-Concomitant treatment of rheumatoid arthritis with anti-TNF-α antibodies and methotrexate 7. U.S. Pat. No. 10,113,198B2-Genetic polymorphisms associated with rheumatoid arthritis, methods of detection and uses thereof |
| Grave's disease: Improvement in thyroid secretion, eye disease | 1. U.S. Pat. No. 9,751,940B2-Epitope regions of a thyrotrophin (TSH) receptor, uses thereof and antibodies thereto |
| Lupus: monitored by SELENA SLEDAI scores. Improvement in these scores is what we want with therapy | 1. U.S. Pat. No. 8,828,998B2-Treatment of lupus, fibrotic conditions, and inflammatory myopathies and other disorders using PI3 kinase inhibitors 2. US20200283499A1-Use of an antibody specific for BDCA 2 for ligation and removal of dendritic cells in the treatment systemic lupus erythematosus 3. U.S. Pat. No. 9,605,066B2-Humanized anti-IL-10 antibodies for the treatment of systemic lupus erythematosus (SLE) 4. USRE48370E1-Levels of BCMA protein expression on B cells and use in methods of treating systemic lupus erythematosus |

-continued

| Diseases | Patent No. and Name |
|---|---|
| | 5. US20170165266A1-Use of 3-(5-amino-2-methyl-4-oxoquinazolin-3(4h)-yl)piperidine-2,6-dione in treatment of immune-related and inflammatory diseases<br>6. US20200209237A1-Detection and treatment of autoimmune disorders<br>7. U.S. Pat. No. 9,907,765B2-Treatment of connective tissue diseases of the skin<br>8. US20200222413A1-Methods of treatment using selective bcl-2 inhibitors |
| Multiple Sclerosis: Improvements in mobility, pain, numbness, tingling, fatigue, depression, anxiety etc. | 1. US20170333418A1-Treatment of multiple sclerosis with combination of laquinimod and fingolimod<br>2. US20210206869A1-Methods for treating progressive multiple sclerosis<br>3. US20180050031A1-Treatment of Multiple Sclerosis With Combination of Laquinimod and Dimethyl Fumarate<br>4. US20190231848A1-Polypeptides and uses thereof as a drug for treatment of multiple sclerosis, rheumatoid arthritis and other autoimmune disorders<br>5. US20190002575Al-Method for the treatment of multiple sclerosis<br>6. U.S. Pat. No. 10,555,913B2-Cladribine regimen for treating multiple sclerosis- |
| Sjogren's syndrome: Decrease auto antibody formation, inflammation and the symptoms. | 1. U.S. Pat. No. 8,722,632B2-Methods for treating Sjogrens syndrome by administering a soluble CTLA4 molecule<br>2. U.S. Pat. No. 10,864,285B2-Methods for the diagnosis and treatment of Sjögren's syndrome<br>3. US20170087156A1-1-((3s,4r)-4-(3-fluorophenyl)-1-(2-methoxyethyl)pyrrolidin-3-y1)-3-(4-methyl-3-(2-methylpyrimidin-5-y1)-1-phenyl-1h-pyrazol-5-yl)urea as a trka kinase inhibitor |
| Ankylosing spondylitis: : Improvements in AS40 scores and the flare of the disease | 1. US20160251424A1-Uses and Compositions for Treatment of Ankylosing Spondylitis<br>2. U.S. Pat. No. 8,926,975B2-Method of treating ankylosing spondylitis<br>3. US20210177966A1-Methods of treating ankylosing spondylitis using il-17 antagonists |
| Guillian Barre Syndrome: Improvement in pain, vision, gait, tingling sensation and various other symptoms. | 1. US20200131245A1-Treating inflammation with soluble hybrid fcgamma receptors<br>2. U.S. Pat. No. 6,972,290B2-Piperazine derivatives and their use as anti-inflammatory agents |
| Type 1 Diabetes: Anti-cd3 antibody, (Tzield-Teplizumab) | 1. WO2023/044495 (PCT/US2022/076702)-Methods for prognosing type 1 diabetes treatments.<br>2. WO2023/039295 (PCT/US2022/043383)-Methods and compositions comprising anti-cd3 antibodies and dyrk1a inhibitors for treating diabetes.<br>3. US20220041720-Methods and compositions for preventing type 1 diabetes. |

Example 1: Histological and Immunohistochemical Analysis

The pancreas was excised, fixed for 24 h in 10% (v/v) neutral buffered formalin (Sigma-Aldrich, Burlington, MA) then transferred into PBS for 24 h. Samples for histology were then stored in 70% (v/v) ethanol for 24 h prior to embedding in paraffin blocks. Sections (5 μm) were cut (Leica 5538 Microtome, Leica Biosystems, Wetzlar, Germany) and rehydrated with xylene 100% (v/v) and ethanol 100% (v/v). Antigens were retrieved by heating the samples (100° C., 30 min) with sodium citrate buffer (10 mM, pH 6). Endogenous peroxidase activity was inhibited using a peroxidase blocking solution (0.3% v/v) for 10 min followed by incubation for 1 h at room temperature with 10% (v/v) goat serum (20 mM Tris, 150 mM NaCl, 0.05% (v/v) Tween 20, pH 7.4 (TBST)). The samples were incubated at 4° C. overnight with a primary insulin antibody (1:1000 dilution, Cell Signaling Technologies, Danvers, MA, USA) then treated for 30 min at room temperature with an anti-rabbit HRP conjugate secondary antibody (undiluted) and DAB+ chromogen for 10 min (EnVision+ System HRP kit Dako, Agilent Technologies, Santa Clara, CA). Sections were counterstained with Harris' Haemotoxylin (Leica Biosystems) then dehydrated with xylene 100% (v/v) and ethanol 100% (v/v). The sections were mounted using dibutylphthalate polystyrene xylene (DPX) and visualized using a Aperio-XT Slide Scanner (Assa Abloy, Stockholm, Sweden). Total tissue area was quantified using the haemotoxylin threshold via the tissue detection feature in Qupath. Staining was quantified manually following threshold normalization. It has been shown in FIG. 1-4.

Example 2: D6PV does not Impair Naïve T Cell Activation

Figure 5:
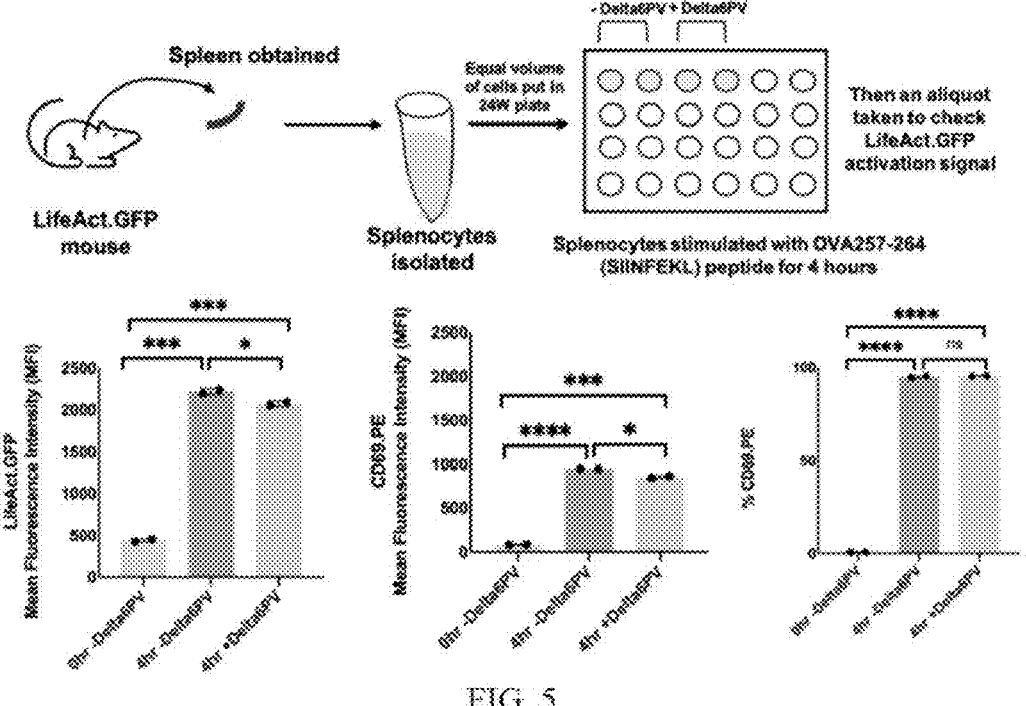
FIG. 5: shows D6PV does not impair naïve T cell activation.

Splenocytes were isolated from OT-I x Lifeact-EGFP mice (Galeano Niño J. L. et al. J. Cell Sci. 2020) and then stimulated for 4 h with cognate antigen (OVA257-264 SIINFEKL) following which T cell activation was quantified based on Lifeact-GFP intensity (c.f. above paper that shows this is a reliable T cell activation reporter) and CD69 upregulation (classical T cell activation marker). Lifeact-GFP signal and CD69 both significantly increased following naïve T cell stimulation-irrespective of D6PV treatment as shown in FIG. 5.

Example 3: D6PV does not Impair Primary Murine T Cell Cytotoxicity

Splenocytes isolated as per above were expanded and differentiated into CD8+ cytotoxic T cells in the presence of IL-2 over 6-7 days, then employed in an immunological cytotoxity assay, were T cells are co-incubated with cognate antigen-presenting tumour cells and bystander tumour cells in a 1:1:1 ratio for 4 hr, and specific killing measured. Treatment with D6PV did not impair antigen-specific cytotoxicity by T cells, whether these were only treated with D6PV during the experiment, or pre-treated during the final days of expansion. When only target and bystander cells were treated with D6PV, no specific killing was observed, showing that D6PV does not per se induce specific cytotoxicity.

CD8+ T cells (untreated or treated with Delta6PV 48 hr before cytotoxicity assay), target cells (EL4.OVA-mCherry), non-target cells (EL4) were mixed at a 1:1:1: ratio and the distribution of the three cell populations was measured by flow cytometry at 4 hr.

Figure 6:
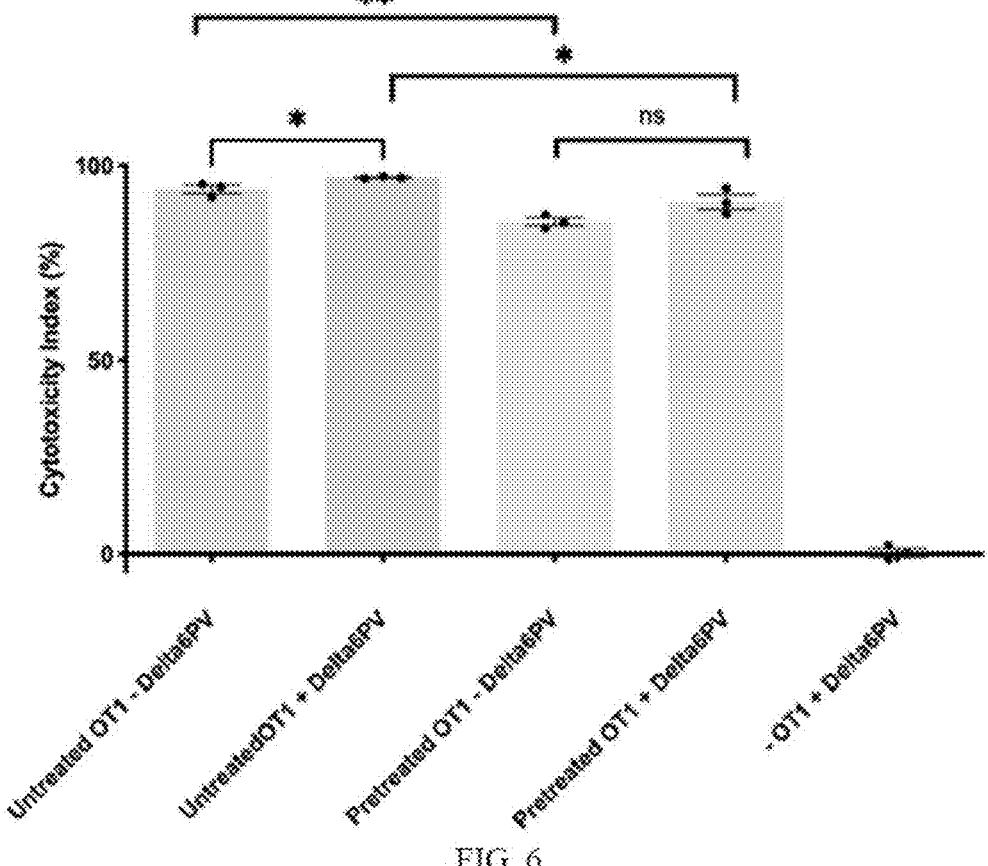
FIG. 6: shows D6PV does not impair primary murine T cell cytotoxicity. Untreated: no D6PV pre-treatment, Pre-treated: D6PV applied for the last 48-72 h of expansion. + or − Delta6PV: whether treatment was applied during the 4 h cytotoxicity experiment or not.]

In FIG. 6, Untreated: no D6PV pre-treatment, Pretreated: D6PV applied for the last 48-72 h of expansion. + or − Delta6PV: whether treatment was applied during the 4 h cytotoxicity experiment or not.

Example 4: D6PV Significantly Restricts Primary Murine T Cell Expansion

Figure 7:
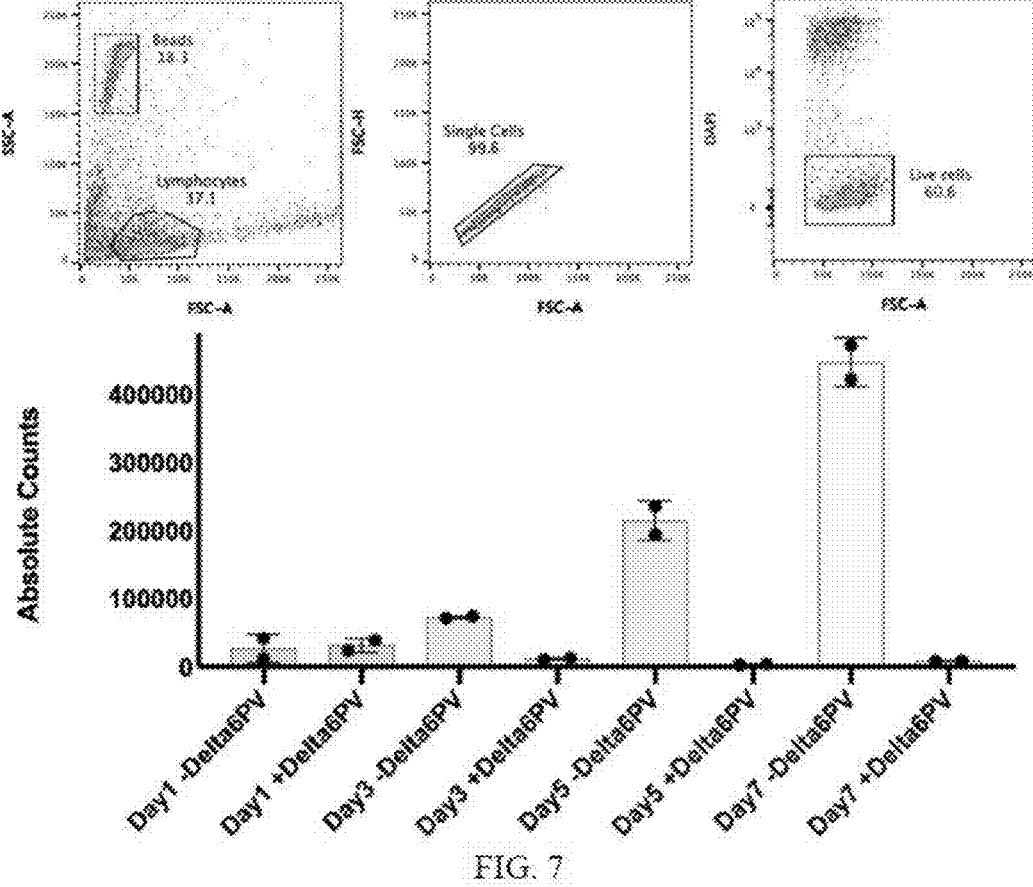
FIG. 7: shows gating strategy for counts and an absolute count.

Splenocytes were isolated from mice, stimulated with cognate SIINFEKL peptide and then expanded over 7 days in the presence of IL-2, with or without D6PV, and then absolute counts were obtained by flow cytometry using Spherotech AccuCount Beads (Spherotech, Chicago, IL, USA) as shown in FIG. 7.

Figure 8:
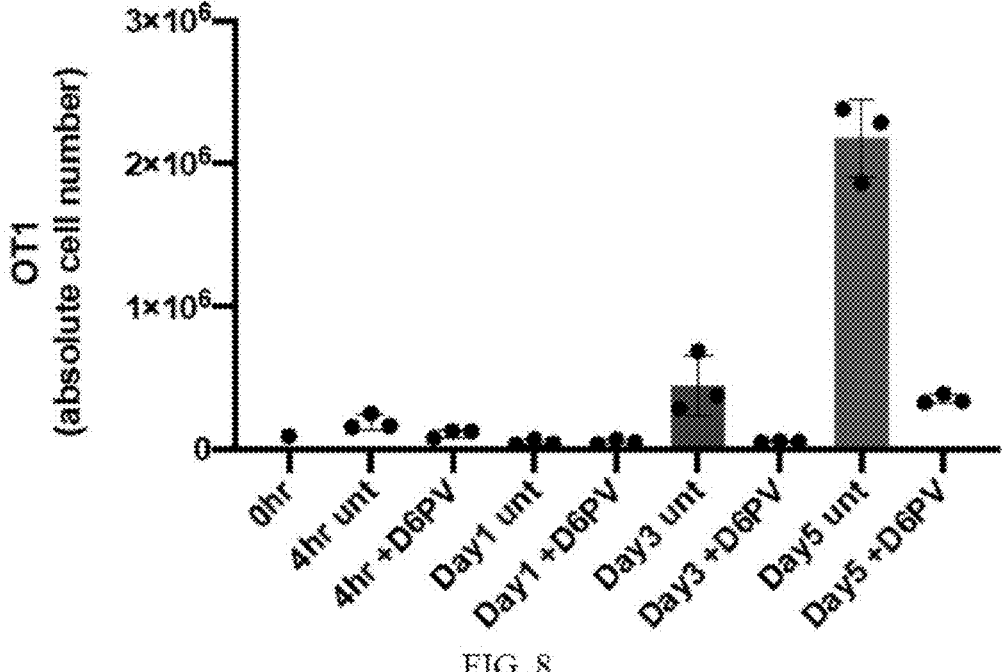
FIG. 8: shows absolute count of OT-I CD8+ T cells.

In a $2^{nd}$ experiment, OT-I CD8+ T cells were counted specifically, with same observation. Note that in above absolute counts, >95% of cells are CD8+ T cells by day 3. (Unt: untreated) as shown in FIG. 8.

Figure 9:
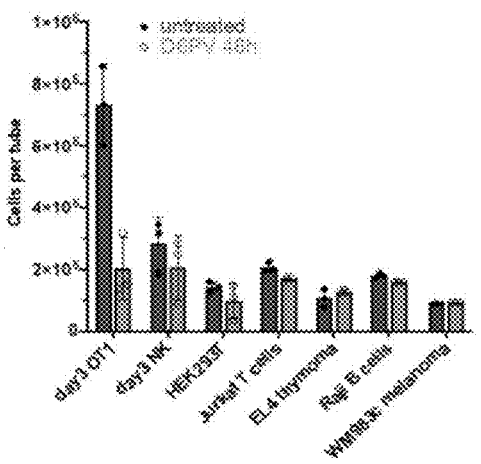
FIG. 9: shows the inhibitory effect of D6PV on expansion is specific to T cells.

Example 5: The Inhibitory Effect of D6PV on Expansion is Specific to Primary T Cells D6PV treatment inhibits primary CD8 T cell expansion over 48 h with minimal effects on proliferation of cell lines (and primary NK cells). OT1: primary murine T cells isolated from mice as per above. Primary NK cells were isolated from C56BL/7 mice as shown in FIG. 9.

Figure 10:
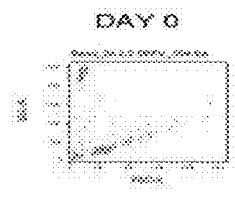
FIG. 10: shows human $CD4^+$ and $CD8^+$ T cell expansions are severely inhibited by D6PV.
Figure 11:
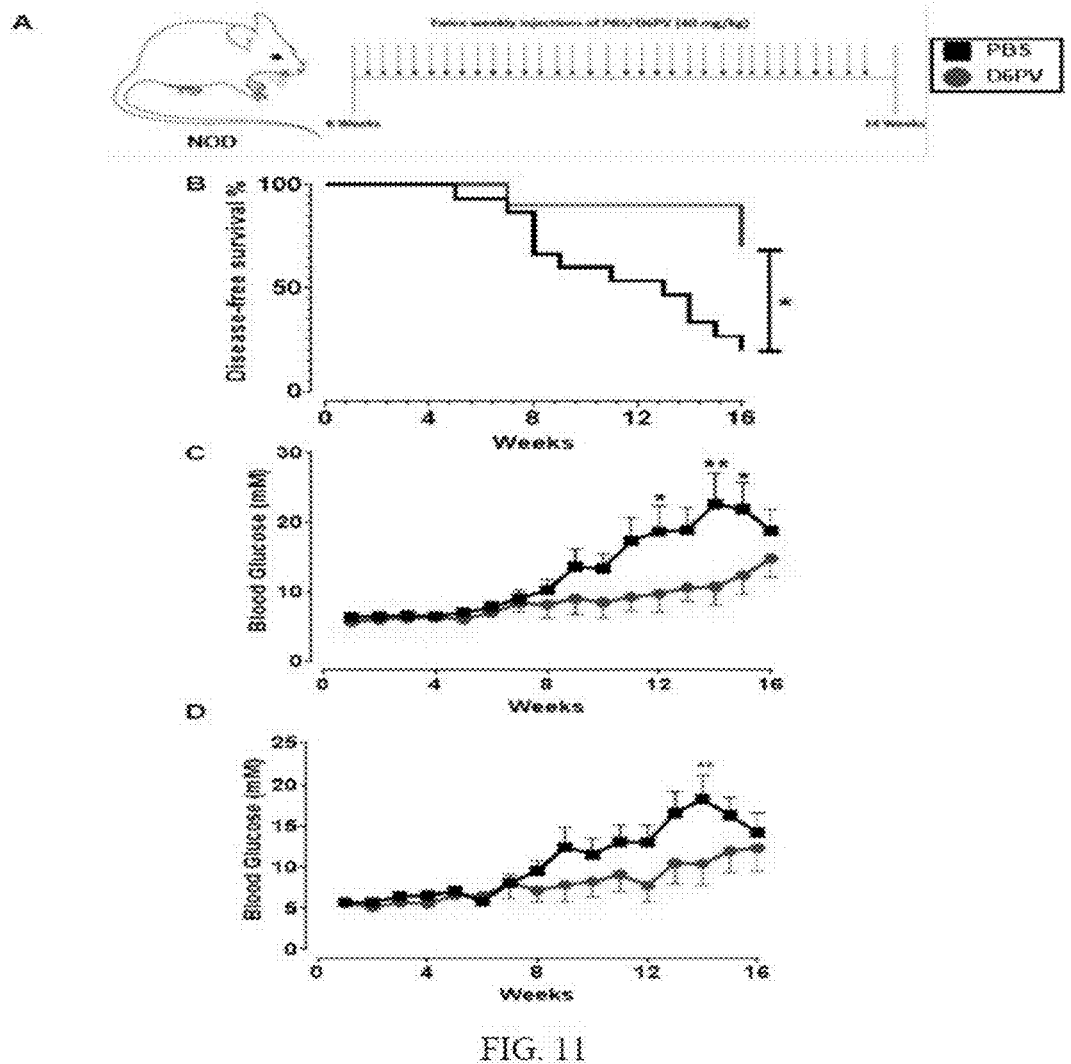
FIG. 11: shows D6PV treatment delays the onset of a diabetic phenotype in NOD mice and decreases fed and fasting blood glucose levels. (A) 8-week-old NOD were randomised to receive D6PV (40 mg/kg, i.p) or an equal volume of PBS (i.p) twice weekly for 16 weeks. (B) The onset of diabetes was determined by two consecutive fed blood glucose readings >13.5 mM over two consecutive days. Data is displayed as a Kaplan-Meier Survival curve. (C) represents fed blood glucose levels and (D) represents 5 h fasted blood glucose levels. Results are presented as mean±SEM and analysed using 2-way ANOVA-mixed effect analysis and Log-rank (Mantel-Cox) test where appropriate. * $p<0.05$, ** $p<0.01$.
Figure 12:
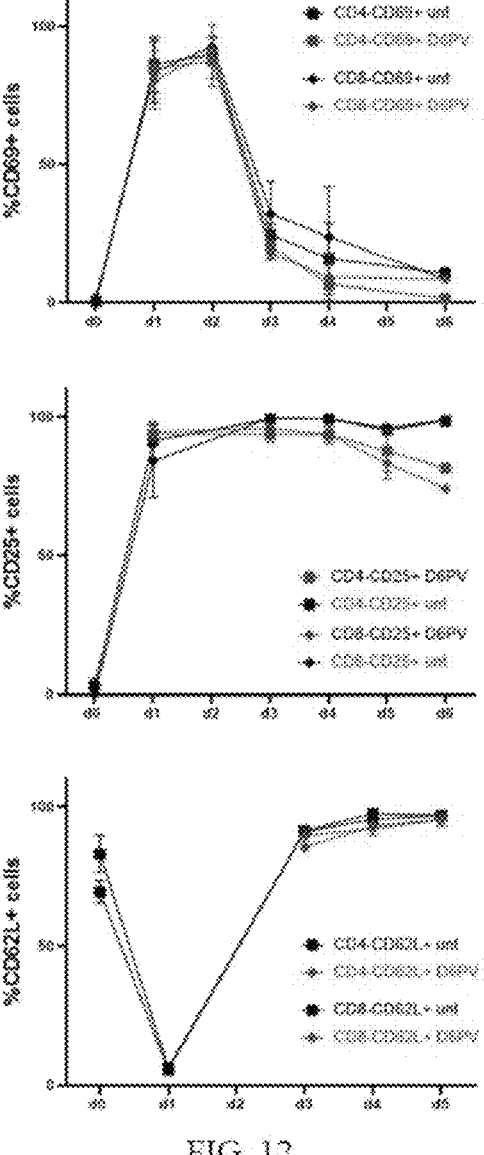
FIG. 12 shows D6PV treatment did not impact the transient activation (CD69), sustained activation (CD25) or activation/central memory (CD62L) of primary human T cells.

Example 6: Human CD4+ and CD8+ T Cell Expansions are Severely Inhibited by D6PV D6PV treatment profoundly inhibits both IL-2 or IL-7/IL-15 driven expansion of primary human T cells stimulated by anti-CD3/CD28 beads. This shows that the suppressive effect is not mediated via the interleukin receptors eg. CD25, CD127, CD122 as shown in FIG. 10.

CD8 T cells more severely impacted than CD4, resulting in skewed CD4/CD8 ratios from day 4 onwards D2-D8 designate days post-isolation from mice.

All references, including granted patents and patent application publications, referred herein are incorporated herein by reference in their entirety.

What is claimed is:

1. A method to delay onset of a disease, comprising: taking a composition comprising Delta6PV, and administering an effective amount of the composition into a subject, wherein the disease comprises type 1 diabetes, wherein the subject is a human or an animal, wherein the Delta6PV in the subject:

(a) delays onset of infiltration of immune cells into islets;

(b) does not impair T cell cytotoxicity; and (c) inhibits IL-2 driven expansion of primary T cells.

2. The method of claim 1, wherein the Delta6PV inhibits IL-7, and/or IL-15 driven expansion of primary T cells in the subject.

3. The method of claim 1, wherein the Delta6PV inhibits primary CD8+ T cell expansion in the subject.

4. The method of claim 1, wherein the Delta6PV does not impair antigen-specific cytotoxicity by T cells in the subject.

5. The method of claim 1, wherein Delta6PV does not impair naïve T cell activation.

6. The method of claim 1, wherein Delta6PV increases islet insulin content in the subject.

7. The method of claim 1, wherein the Delta6PV inhibits IL-7 driven expansion of primary T cells in the subject.

8. The method of claim 1, wherein the Delta6PV inhibits IL-15 driven expansion of primary T cells in the subject.

9. The method of claim 1, wherein the composition further comprises at least one pharmaceutical acceptable carrier.

10. The method of claim 1, wherein the composition optionally includes adjuvant.

11. A method to treat a disease, comprising: taking a composition comprising Delta6PV, and administering an effective amount of the composition into a subject, wherein the disease comprises type 1 diabetes, wherein the Delta6PV in the subject inhibits IL-2 driven expansion of primary human T cells, and wherein the subject is a human or an animal.

12. The method of claim 11, wherein the Delta6PV inhibits IL-7, and/or IL-15 driven expansion of primary T cells in the subject.

13. Method of claim 11, wherein the Delta6PV inhibits primary CD8+ T cell expansion in the subject.

14. The method of claim 11, wherein the Delta6PV impairs antigen-specific cytotoxicity by T cells in the subject.

15. The method of claim 11, wherein the Delta6PV increases islet insulin content in the subject.

16. The method of claim 1, wherein Delta6PV does not impair naïve T cell activation.

17. The method of claim 11, wherein the Delta6PV inhibits IL-7 driven expansion of primary T cells in the subject.

18. The method of claim 11, wherein the Delta6PV inhibits IL-15 driven expansion of primary T cells in the subject.

19. The method of claim 11, wherein the composition further comprises at least one pharmaceutical acceptable carrier.

* * * * *